United States Patent [19]

Teves

[11] Patent Number: 5,309,905
[45] Date of Patent: May 10, 1994

[54] CONNECTOR FOR ENDOTRACHEAL TUBES

[75] Inventor: Leonides Y. Teves, Bradenton, Fla.

[73] Assignee: Advanced Medical Concepts, Inc., Bradenton, Fla.

[21] Appl. No.: 896,257

[22] Filed: Jun. 10, 1992

[51] Int. Cl.$^5$ .............................................. A61M 16/00
[52] U.S. Cl. ................................ 128/207.14; 128/912; 128/DIG. 26
[58] Field of Search ....................... 128/200.24, 202.27, 128/912, DIG. 26, 203.12, 207.14, 200.24, 202.27, 912, DIG. 26

[56] References Cited

U.S. PATENT DOCUMENTS

| | | | |
|---|---|---|---|
| 4,291,691 | 9/1981 | Cabal et al. | 128/912 |
| 4,612,929 | 9/1986 | Schubert et al. | 128/912 |
| 4,621,634 | 11/1986 | Nowacki et al. | 128/912 |
| 4,674,496 | 6/1987 | Svadjian et al. | 128/912 |
| 4,967,759 | 11/1990 | Teves | 128/715 |
| 4,995,387 | 2/1991 | Jinotti | 128/912 |

Primary Examiner—David A. Wiecking
Assistant Examiner—Aaron J. Lewis
Attorney, Agent, or Firm—Joseph C. Mason, Jr.; Ronald E. Smith

[57] ABSTRACT

A connector for joining an endotracheal tube and an integrally formed auxiliary lumen to a source of anesthesia and a preselected item of auxiliary equipment, respectively, includes a first pair of tubular mounting members on a proximal end of the connector that are closely radially spaced with respect to one another and longitudinally spaced from a second pair of tubular mounting members on a distal end of the connector that are closely radially spaced with respect to one another. A pair of parallel bores are formed in the base of the connector to provide fluid communication between associated, longitudinally spaced apart mounting members. The radially spaced mounting members on the proximal end slide-fittingly receive the respective distal ends of an anesthesia supply tube and an auxiliary monitoring equipment tube, and the radially spaced mounting members on the distal end slide-fittingly receive the respective proximal ends of an endotracheal tube and an auxiliary lumen that is formed integrally with the endotracheal tube. The endotracheal tube and lumen share a common length.

1 Claim, 1 Drawing Sheet

CONNECTOR FOR ENDOTRACHEAL TUBES

BACKGROUND OF THE INVENTION

1. Field of the Invention

This invention relates, generally, to endotracheal tubes of the type having an auxiliary lumen. More particularly, it relates to a connector therefor.

2. Description of the Prior Art

U.S. Pat. No. 4,967,759 to the present inventor discloses an endotracheal tube having an auxiliary lumen integrally formed therewith along the extent thereof.

Due to the close spacing of the auxiliary lumen and the main endotracheal tube, connection of the auxiliary lumen to preselected auxiliary equipment and connection of the main endotracheal tube to a supply source for the gaseous fluids to be administered to the patient is problematic. Note that a total of four items must be interconnected, i.e., the auxiliary equipment must be connected to the auxiliary lumen, and the supply source of the gas must be connected to the main endotracheal tube. The connector currently in use is designed to interconnect the proximal end of the main endotracheal tube and the distal end of a tube from said anesthesia supply source; no means are provided for interconnecting the auxiliary equipment and the auxiliary lumen. Thus, the proximal end of the auxiliary lumen merely abuts the connector when the proximal end of the endotracheal tube is connected to said connector. This results in a very unsatisfactory interconnection of the auxiliary equipment and the auxiliary lumen; the connector at the distal end of the tubing extending from the auxiliary equipment is brought around the endotracheal tube connector and brought into connection with the proximal end of the auxiliary lumen. A sharp bend must be formed where the tubing from the auxiliary equipment meets the proximal end of the auxiliary lumen, resulting in an unacceptable constriction. Moreover, this arrangement requires the use of two separate connectors. Since connectors are bulky, each connector interferes with the other when the various tubes are interconnected.

In the above-referenced patent, this problem was overcome by making the auxiliary lumen substantially shorter than the main endotracheal tube so that the bend could be more gradual, thereby eliminating the constriction. However, this was unsatisfactory for other reasons. Specifically, the main endotracheal tube and auxiliary lumen are best constructed as a single unit. Thus, the manufacturing process is simpler and thus more cost effective if the main endotracheal tube and the auxiliary tube have a common length. Truncating the auxiliary lumen so that its proximal end is remote from the main connector thus drives up the manufacturing costs associated with the patented item. Moreover, shortening of the lumen still requires use of two connectors.

What is needed, then, is a way to interconnect the lumen and the main tube to their respective pieces of equipment with a single connector and in the absence of sharp bends or truncated lumens. However, at the time the present invention was made, the prior art, when considered as a whole as required by law, neither taught nor suggested to those of ordinary skill in this field how the extant problems could be resolved.

SUMMARY OF THE INVENTION

An improved connector includes an auxiliary pair of fittings on its proximal and distal faces, in addition to the conventional fittings for connection of the main endotracheal tube and the supply of anesthesia, so that the main endotracheal tube and the auxiliary lumen may be manufactured as a single unit with the length of the auxiliary lumen being coextensive with the length of the main endotracheal tube. The auxiliary fitting on the proximal face of the novel connector receives the distal end of the auxiliary line from the auxiliary equipment, and the auxiliary fitting on the distal face of the connector provides a mount for the proximal end of the auxiliary lumen. This arrangement of parts also eliminates any bends in the line from the auxiliary equipment and in the auxiliary lumen.

It is therefore understood that the primary object of this invention is to advance the art of endotracheal tubes in general.

Another broad object is to advance the art of connectors in general.

A more specific object is to provide an improved connector that combines connection means for four separate items in a single unit.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

Similar reference numerals refer to similar parts throughout the several views of the drawings.

DETAILED DESCRIPTION OF THE PREFERRED EMBODIMENT

Figure 1:
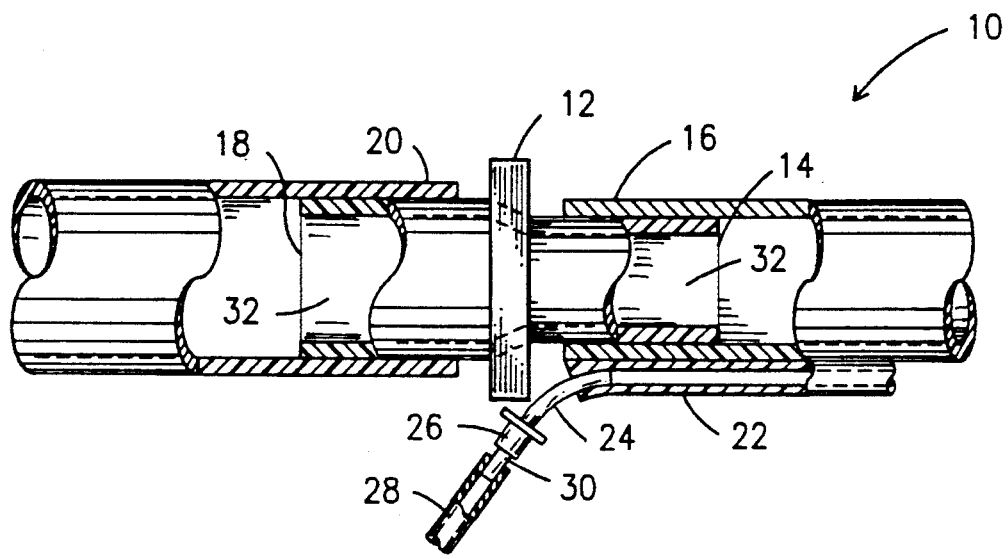
FIG. 1 is a side sectional view of a prior art connector.

FIG. 1 depicts a prior art assembly; it is denoted 10 as a whole and includes main connector 12 that includes distal tubular projection or mounting member 14 onto which the proximal end of the main endotracheal tube 16 is slide-fittingly press fit and proximal tubular projection or mounting member 18 onto which the distal end of tube 20 is slide-fittingly press fit. Tube 20 delivers the anesthesia from a source thereof to the proximal end of connector 12, and main endotracheal tube 16 delivers said anesthesia to the patient's lungs.

Auxiliary lumen 22 is formed integral with main tube 16 as described in the present inventor's earlier patent as above-mentioned. Its proximal end tightly slide-fittingly receives tubular projection 24 of connector 26; note that the proximal end of auxiliary lumen 22 is slightly distorted by said projection 24 due to the interference between connectors 12 and 26. The distal end of an auxiliary tube 28 slide-fittingly engages tubular projection 30 of connector 26; tube 28 extends to pressure-sensing means, temperature sensing means, acoustical means, or other monitoring devices as explained in said patent.

Figure 2:
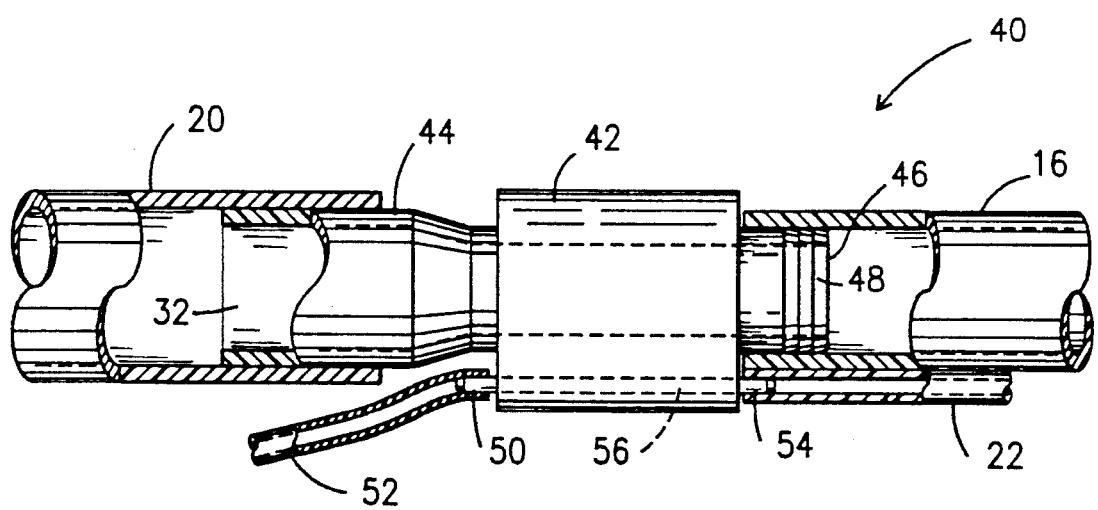
FIG. 2 is a side sectional view of the novel connector.

The improved assembly is shown in FIG. 2 and is denoted 40 as a whole. It includes novel connector 42 having generally tubular mounting member 44 extending from the proximal end thereof and its associated tubular mounting member 46 extending from the distal end thereof. Bore 32, formed in the base of the novel connector 42, provides fluid communication between mounting members 44 and 46. In the claims that follow, mounting members 44 and 46 are referred to as the first and third tubular projections, respectively. The distal end of anesthesia supply tube 20 slidingly press-fittingly engages mounting member 44 and the proximal end of main endotracheal tube 16 slidingly press-fittingly engages mounting member 46 as shown. Plural annular ridges 48 increase the frictional engagement between tube 16 and mount 46.

An auxiliary mounting member 50 is provided on the proximal end of connector 42, and the distal end of auxiliary tube 52 is slidingly and press-fittingly engaged thereto. Another auxiliary mounting member 54 is provided on the distal side of connector 42, and the proximal end of auxiliary lumen 22 is similarly secured thereto. Bore 56, formed in base 42 in parallel relation to bore 32, provides fluid communication between mounting members 50 and 54. In the claims that follow, these auxiliary mounting members are referred to as the second and fourth tubular projections, respectively. Bore 56 provides open communication between the auxiliary equipment at the proximal end of auxiliary tube 52 and lumen 22. Note that the bend shown in FIG. 1 has been eliminated, and that the second connector shown in FIG. 1, connector 26, is also eliminated, thereby achieving the objects of this invention.

Note further that first and second fittings 44, 50 are closely radially spaced with respect to one another, as are the third and fourth fittings 46, 54.

Novel connector 40 is preferably made in a single, integrally formed piece, but it may be manufactured in two or more pieces. It is preferably made of the same materials as the connectors heretofore known.

This invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, What is claimed is:

1. A connector, comprising:
   a base member of predetermined longitudinal extent having a proximal end and a distal end;
   a first tubular projection, having a predetermined diameter, disposed on said proximal end of said base member;
   a second tubular projection, having a predetermined diameter, disposed on said proximal end of said base member;
   said predetermined diameter of said first tubular projection being substantially greater than the predetermined diameter of said second tubular projection;
   said first and second tubular projections being disposed in closely spaced parallel relation to one another;
   a third tubular projection, having a predetermined diameter, disposed on said distal end of said base member;
   a fourth tubular projection, having a predetermined diameter, disposed on said distal end of said base member;
   said predetermined diameter of said third tubular projection being substantially greater than the predetermined diameter of said fourth tubular projection;
   said second and fourth tubular projections being disposed in closely spaced parallel relation to one another;
   a first bore means formed in said base member for providing fluid communication between said first and third tubular projections;
   a second bore means formed in said base member for providing fluid communication between said second and fourth tubular projections;
   said first and second bore means being disposed in parallel relation to one another;
   said first tubular projection disposed in axial alignment with said third tubular projection;
   said second tubular projection disposed in axial alignment with said fourth tubular projection;
   an anesthesia supply tube;
   an auxiliary tube;
   an endotracheal tube;
   an auxiliary lumen integrally formed with said endotracheal tube;
   said anesthesia supply tube being releasably connected to said first tubular projection and said auxiliary tube being releasably connected to said second tubular projection;
   said endotracheal tube being releasably connected to said third tubular projection and said auxiliary lumen being releasably connected to said fourth tubular projection;
   whereby a single connector interconnects said anesthesia supply tube to said endotracheal tube and said auxiliary tube to said auxiliary lumen and wherein said anesthesia supply tube, endotracheal tube, auxiliary tube, and auxiliary lumen are substantially free of constrictions.

* * * * *